US007084627B2

(12) United States Patent
McKendry et al.

(10) Patent No.: US 7,084,627 B2
(45) Date of Patent: Aug. 1, 2006

(54) METHOD FOR TRIGGERING NMR MEASUREMENT IN A NMR CHECK WEIGHING SYSTEM

(75) Inventors: James M McKendry, Headington (GB); Robert Selway, Kidlington (GB); Nicholas John Collier, Burwell (GB); Valerie Anne Scott, Cambridge (GB); Jozef A. W. M. Corver, Neunen (NL); Paulus C. J. M. Hendrickx, Baarle-Nassau (NL)

(73) Assignee: The BOC Group, Inc., Murray Hill, NJ (US)

( * ) Notice: Subject to any disclaimer, the term of this patent is extended or adjusted under 35 U.S.C. 154(b) by 0 days.

(21) Appl. No.: 10/836,299

(22) Filed: Apr. 30, 2004

(65) Prior Publication Data

US 2005/0242809 A1 Nov. 3, 2005

(51) Int. Cl.
*G01V 3/00* (2006.01)

(52) U.S. Cl. ...................... 324/308; 324/307; 324/309; 324/314

(58) Field of Classification Search ........ 324/300–322; 364/551.01; 177/1

See application file for complete search history.

(56) References Cited

U.S. PATENT DOCUMENTS 3,796,873 A 3/1974 Ledgett
4,727,325 A 2/1988 Matsui et al.
5,015,954 A 5/1991 Dechene et al.
5,049,819 A 9/1991 Dechene et al.
5,291,422 A 3/1994 Esztergar
5,302,896 A 4/1994 Dechene et al.
5,684,399 A * 11/1997 Bayer ......................... 324/306
6,028,428 A 2/2000 Cunningham et al.
6,362,619 B1 3/2002 Prammer et al.
6,377,049 B1 4/2002 Benz et al.

(Continued)

FOREIGN PATENT DOCUMENTS

DE 1803372 A1 5/1970

(Continued)

OTHER PUBLICATIONS

Derwent WPI Abstract, UNILEVER NV, Package Weight Measuring System, NL 154001B, Jul. 15, 1977 (Corresponds to DE 1803372A1).

(Continued)

*Primary Examiner*—Diego Gutierrez
*Assistant Examiner*—Tiffany A. Fetzner
(74) *Attorney, Agent, or Firm*—Ira L. Zebrak; Bernard Lau

(57) ABSTRACT

Magnetic resonance methods are provided for determining the mass of samples in vials (1) in a production line, each sample having a net magnetisation capability, including the steps of applying a first magnetic field in a first direction in an interrogation zone (25) for creating a net magnetisation within a sample located within the interrogation zone (25), applying an alternating magnetic field in a second direction in the interrogation zone (25) for temporarily changing the net magnetisation of the sample located within the interrogation zone (25), monitoring energy emitted by the sample as the net magnetisation of the sample returns to its original state and generating an output signal whose current amplitude is proportional to the energy emitted, comparing the current amplitude with like data obtained from at least one similar sample of known mass, and determining the mass of the sample. The step of applying an alternating magnetic field includes the step of triggering application of the alternating magnetic field when the sample is located at a position ($P_M$) within the interrogation zone (25) with the current amplitude at its maximum.

14 Claims, 3 Drawing Sheets

U.S. PATENT DOCUMENTS

| | | | | |
|---|---|---|---|---|
| 6,426,058 | B1 | 7/2002 | Pines et al. | |
| 6,479,994 | B1 | 11/2002 | Hills et al. | |
| 6,549,007 | B1 | 4/2003 | Hills et al. | |
| 6,759,601 | B1 * | 7/2004 | Petty et al. | 177/1 |
| 6,946,838 | B1 * | 9/2005 | Corver et al. | 324/307 |
| 7,002,346 | B1 * | 2/2006 | Schaepman et al. | 324/315 |
| 2004/0231699 | A1 * | 11/2004 | Corver | 134/3 |
| 2004/0251904 | A1 * | 12/2004 | Corver et al. | 324/321 |
| 2005/0116712 | A1 * | 6/2005 | Corver et al. | 324/309 |
| 2005/0122104 | A1 * | 6/2005 | Corver et al. | 324/309 |
| 2005/0242808 | A1 * | 11/2005 | McKendry et al. | 324/307 |
| 2005/0242811 | A1 * | 11/2005 | Schaepman et al. | 324/315 |
| 2005/0242813 | A1 * | 11/2005 | Aptaker et al. | 324/318 |
| 2005/0247493 | A1 * | 11/2005 | Aptaker et al. | 177/1 |

FOREIGN PATENT DOCUMENTS

| | | | |
|---|---|---|---|
| GB | 2149509 | A | 6/1985 |
| WO | WO 99/67606 | A1 | 12/1999 |
| WO | WO 2004104600 | A2 * | 12/2004 |

OTHER PUBLICATIONS

PCT International Search Report of International Application No. PCT/US04/20889; Date of mailing of International Search Report: Mar. 22, 2005.

PCT Written Opinion of the International Searching Authority of International Application No. PCT/US04/20889; Date of mailing: Mar. 22, 2005.

* cited by examiner

METHOD FOR TRIGGERING NMR MEASUREMENT IN A NMR CHECK WEIGHING SYSTEM

FIELD OF THE INVENTION

The present invention relates to check weighing material in a container, while the container is moving in a production line, using nuclear magnetic resonance (NMR) techniques. More particularly, the present invention relates to a method for determining when an NMR measurement is to be triggered to check weigh the material in a particular container.

BACKGROUND

The use of NMR techniques in measurement, detection and imaging has become desirable in many scientific fields of endeavor. The non-invasive, non-destructive nature of NMR has facilitated application to industrial instrumentation, analysis and control tasks, in a variety of applications, including but not limited to cosmetics, perfumes, industrial chemicals, biological samples and food products. As one example, check weighing is used by the pharmaceuticals industry for monitoring and regulating the amount of drug in a sealed glass vial during filling. The drug weight can be as small as a fraction of a gram, and is required to be weighed with an accuracy of a few percent or better, in a vial weighing tens of grams at a rate of several weighings per second.

International Patent Application No. WO 99/67606 (the "'606 application"), incorporated herein by reference as if fully written out below, describes a check weighing system for samples on a production line using NMR techniques. This system includes a magnet for creating a static magnetic field over an interrogation zone to produce a net magnetisation within a sample located within the interrogation zone, and an RF coil for applying an alternating magnetic field over the interrogation zone to cause excitation of the sample according to the principles of NMR.

As is well known in the NMR art and noted in the '606 application, successful application of magnetic resonance requires that the sample under test be allowed to reach substantially maximum net magnetisation before the application of any further excitation field. Failure to allow the magnetisation to first fully develop will result in a sample reply signal that is less then maximum, and an inaccurate and imprecise resulting weight. Thus, it is imperative to carefully correlate the position of the sample under test with the triggering of further field excitations, such as by the RF coil.

In the '606 application, triggering occurs when the filled vial is at a desired location within the check weighing station. This, in turn, is determined by detecting the moment in time when the filled vial passes an optical position sensor, and the speed of the conveyor belt carrying the filled vial. In other words, the filled vial position is calculated solely as a function of the product of time and velocity. This does not insure that the position of the filled vial at the time of triggering will result in a maximum sample reply signal.

It is desirable to provide a method for triggering further field excitation in a NMR check weighing system for samples on a production line so that the sample under test is positioned to return the maximum sample reply signal.

SUMMARY

There is provided a magnetic resonance method for determining the mass of samples in a production line, each sample having a net magnetisation capability, comprising the steps of:

- applying a first magnetic field in a first direction in an interrogation zone for creating a net magnetisation within a sample located within the interrogation zone;
- applying an alternating magnetic field in a second direction in the interrogation zone for temporarily changing the net magnetisation of the sample located within the interrogation zone;
- monitoring energy emitted by the sample as the net magnetisation of the sample returns to its original state and generating an output signal having a characteristic which is proportional to the energy emitted;
  - the step of applying an alternating magnetic field including the step of triggering application of the alternating magnetic field when the sample is located at a position within the interrogation zone with the output signal characteristic at its maximum;
- comparing the output signal characteristic with like data obtained from at least one similar sample of known mass; and
- determining the mass of the sample.

There is also provided a method of calibrating a magnetic resonance method for determining the mass of samples in a production line, each sample having a net magnetisation capability, the production line having a magnetic resonance interrogation zone with a first magnetic field and an alternating magnetic field, comprising the steps of:

- performing a nuclear magnetic resonance measurement on the sample at each of a plurality of positions as the sample is moved through the region of the alternating magnetic field prior to production operation of the production line; and
- determining the position of the sample when the sample is located at a position within the interrogation zone with a characteristic of an output signal proportional to the energy emitted by the sample under nuclear magnetic resonance measurement at its maximum.

BRIEF DESCRIPTION OF THE DRAWINGS

FIG. 2 depicts in particular the poles of a static field magnet, RF coils for applying an alternating magnetic field in an interrogation zone, a vial position detection device preceding the interrogation zone, and a conveyor for moving a plurality of samples through the interrogation zone. A plurality of sample positions, $P_s$, are marked on the conveyor belt.

DETAILED DESCRIPTION

Figure 3:
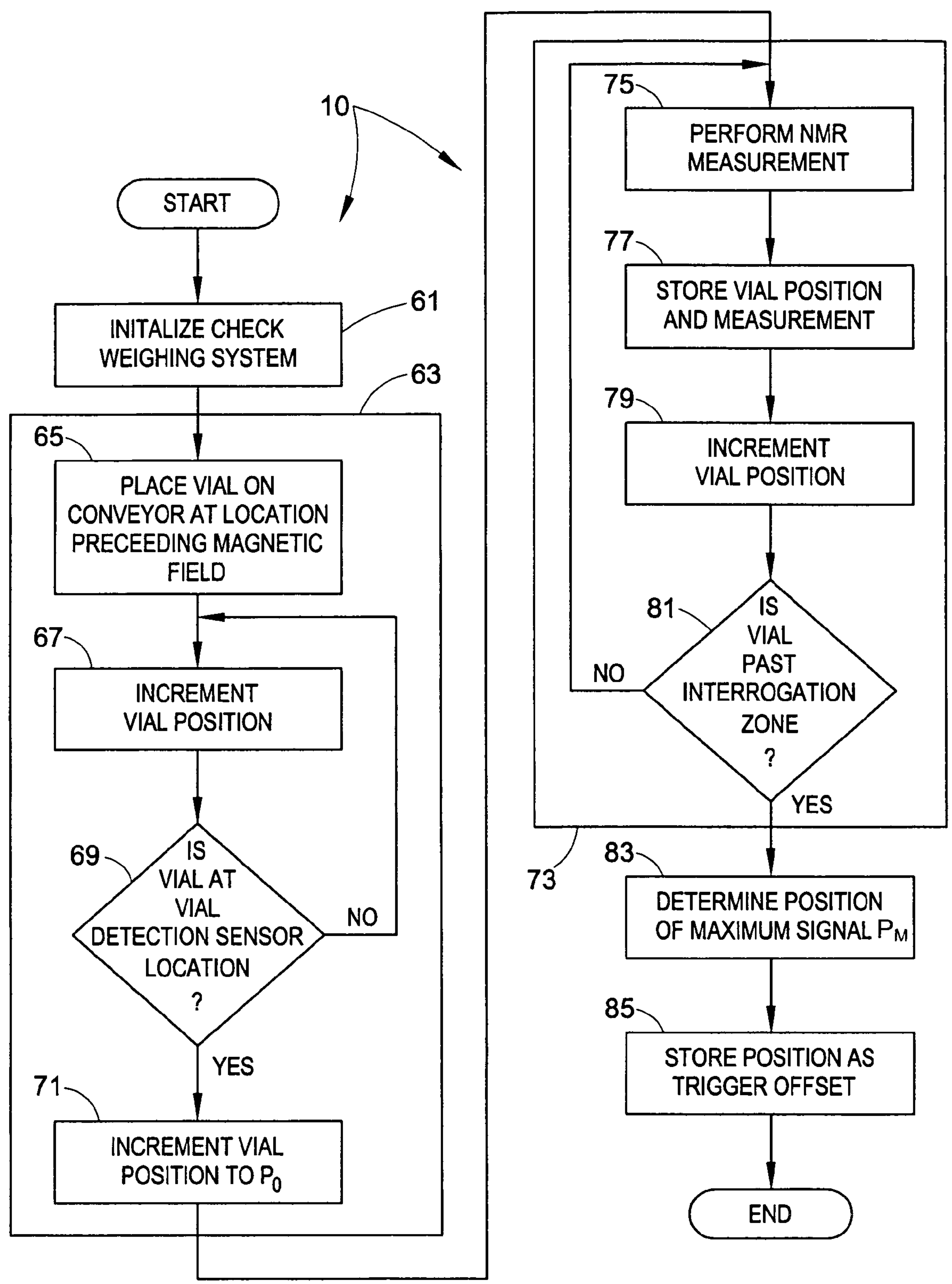
FIG. 3 is a top level flow chart of an exemplary method in accordance with the teachings of the present invention for calibrating the triggering of further field excitation in an NMR check weighing system for samples on a production line when the sample under test is positioned to return the maximum sample reply signal.

A method in accordance with the present invention is indicated generally by the numeral 10 in FIG. 3. In order to understand best this method, it is helpful to first review certain of the structure of an exemplary NMR check weighing system and its associated production line.

Figure 1:
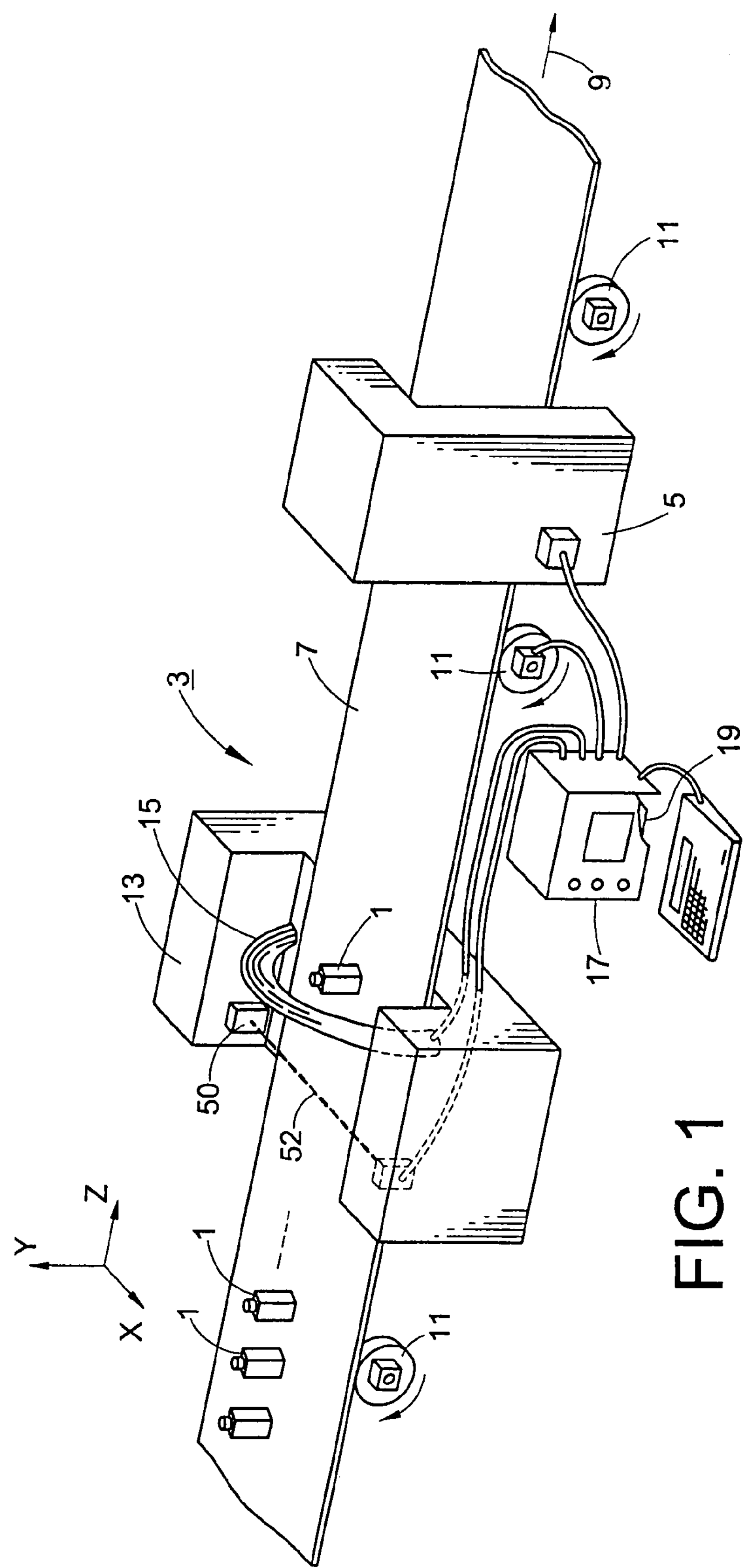
FIG. 1 is a diagrammatic view of a portion of a production line with an exemplary NMR check weighing station for checking that each container passing through the weighing station has the desired amount of product.

FIG. 1 shows a portion of a production line, which fills glass vials 1 with a drug sample. Included is an exemplary weighing station 3 that is provided "in-line"for non-contact weighing of each of the filled non-continuous and discrete samples in vials that pass therethrough, and a reject station 5 that removes those vials from the line that do not have the sufficient amount of the drug to meet product specifications. Vials 1 are transported to weighing station 3 from a filling (and optionally sealing) station (not shown) by a conveyor belt 7 which, as represented by the arrow 9, moves in the z direction through the action of rotating conveyor wheels 11.

Weighing station 3 uses NMR techniques to determine the mass of the drug sample within each of the vials 1. As those ordinarily skilled in the art will appreciate, glass vials are useful as the container, because they do not give a signal that might interfere with the measurement process. In this embodiment, weighing station 3 includes a permanent magnet 13, a radio frequency (RF) coil 15 and a computer control system 17 having a processor 19. Magnet 13 creates a homogeneous direct current (DC) or static magnetic field in the x direction across conveyor belt 7 in a region that may be referred to as the interrogation zone 25. Interrogation zone 25 extends the length of conveyor belt 7 through which the static magnetic field is uniformly applied by permanent magnet 13. The sample in vial 1 contains nuclei which each possess a magnetic moment, e.g. 1H nuclei (protons), as a result of the spin of the nuclei. Because the sample protons posses a magnetic moment, the sample is capable of acquiring a net magnetisation when under the influence of certain magnetic fields. When the sample is within interrogation zone 25, the applied static magnetic field creates a net magnetisation within the sample.

In most NMR systems, the static magnetic field strength is such that the Larmor frequency of the sample is in the radio frequency range of the electromagnetic spectrum. Applying an alternating current (AC) magnetic field to the sample at the sample's Larmor frequency and orientated orthogonal to the static magnetic field, will cause the sample's net magnetisation to rotate about the AC magnetic field's axis, away from the direction of the static field. In this embodiment, this magnetic field is generated by applying a corresponding AC current to the RF coil 15. Varying the amount of energy delivered to the RF coil 15 can vary the angle of rotation of the net magnetisation.

In this exemplified embodiment, an excitation field that causes a 90° rotation is used to excite the sample. After the 90° pulse has been applied to the sample, the sample is left in a high-energy, non-equilibrium state, from which it will relax back to its original state of equilibrium. As it relaxes, electromagnetic energy at the Larmor frequency is emitted, the magnetic component of which induces a sample reply signal in the form of current in the RF coil 15.

RF coil 15 monitors energy emitted by the sample as the net magnetisation of the sample returns to its original state and generates an output signal having a characteristic which is proportional to the energy emitted. In the present example a characteristic of the induced current, i.e., peak amplitude, varies with, among other things, the number of magnetic moments in the sample and hence the number of molecules in the sample. The received signal is then passed to the computer control system 17, which compares the peak amplitude of the signal received from the unknown sample, with the peak amplitude of a signal received from a calibration sample with a known mass (or weight), to determine the unknown mass (or weight) of the production sample being tested. The check weighing station 3 may be able to generate and receive signals at different Larmor frequencies needed to be able to excite different NMR responsive elements in samples. If the computer control system 17 can store calibration data for each of the different samples, then the check weighing station would be able to determine the mass of various samples using a characteristic of the NMR signals from the different NMR responsive elements.

Figure 2:
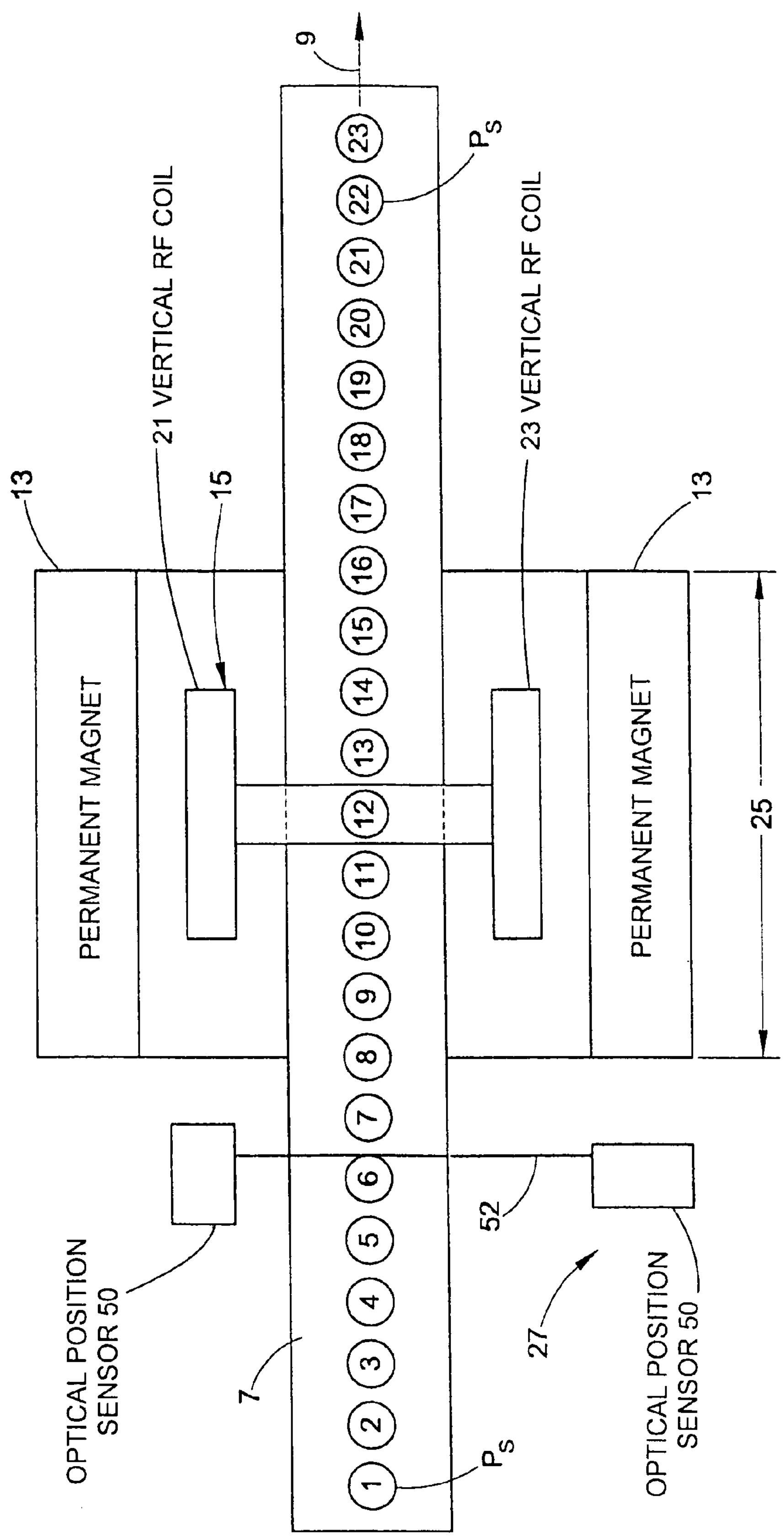
FIG. 2 is a diagrammatic, top view of the portion of the production line with the exemplary NMR check weighing station shown in FIG. 1.

FIG. 2 is a diagrammatic, top view of the exemplary NMR check weighing station 3 shown in FIG. 1. FIG. 2 depicts in particular the poles of static field magnet 13, an RF coil assembly 29 having two vertically mounted RF coils 21 and 23 for applying an alternating magnetic field in an interrogation zone 25, a vial position detection device 27 preceding or at the start of interrogation zone 25 (such as the optical position sensor 50 having a light beam 52), and conveyor belt 7 for moving a plurality of vials 1 through interrogation zone 25. A plurality of vial positions, $P_s$, are marked on conveyor belt 7 with numerals one through twenty-three.

Vial position detection device 27 may be any of the variety of position sensors known to the skilled artisan for accurately and precisely detecting when the desired sample package reaches a known physical position on conveyor belt 7 preceding check weighing station 3. For example, FIG. 2 illustrates an optical position sensor 50 having a light beam 52 that is broken by the leading edge of vial 1 when it moves into position $P_6$, and the sensor is mounted in advance of interrogation zone 25. FIG. 1 depicts an optical position sensor 50 and light beam located at the beginning of interrogation zone 25. Such a location may be preferably for economic or other reasons, although the selected, known physical position could be any location preceding the location of maximum sample reply signal. Irrespective of its position, optical position sensor 50 also may detect passage of the trailing edge of vial 1 when light beam 52 is reestablished. This information may be used to improve measurement by determining more accurately the center of vial 1 and reducing sensor intolerance to the diameter of vial 1.

For illustrative purposes, but not by way of limitation, the general operation of the NMR check weighing system as shown in FIGS. 1 and 2 will be described. First, the check weighing system is initialized, including installing RF probe 29 appropriate for the sample to be tested. Once production is begun, conveyor belt 7 continuously transports vials 1 whose sample mass (or weight) is to be determined. As each vial reaches position P6, its leading edge interrupts light beam 52 causing optical position sensor 50 to generate a signal accurately establishing the position of that vial 1 to computer control system 17. Computer control system 17 then tracks the motion of conveyor belt 7 as vial 1 advances to the position PM within interrogation zone 25 where the sample in vial 1 will return the maximum sample reply signal. At the instant in time when vial 1 is in position PM, a brief energization of RF probe 29 is triggered, applying an alternating magnetic field in interrogation zone 25 such that the net magnetisation of the sample in vial 1 is temporarily changed. RF probe 29 monitors the energy emitted by the sample in vial 1 as the net magnetisation of the sample returns to its original state of equilibrium, and generates an output signal having a characteristic which is representative of and proportional to the energy emitted by the sample, such as current amplitude. Computer control 17 receives the RF probe output signal. Processor 19 compares the current amplitude or other output signal characteristic with like corresponding data obtained from at least one similar sample of known mass, and determines the mass of the sample from the results of the comparison.

The maximum sample reply signal occurs when the selected output signal characteristic achieves its maximum value. The physical position of vial 1 when the characteristic achieves its maximum value may be found by performing a calibration of processor 19 prior to production operation of the production line, such as the exemplary, pre-production calibration method depicted in the flow chart shown in FIG. 3.

First, and before production is begun, in step 61 non-contact check weighing system 3 is initialized in its customary manner, including the installation of an appropriate RF probe 29 suitable for the specific container which will carry the sample whose mass or weight is to be determined. In the present example the container may continue to be the glass vial 1 noted hereinbefore.

Next, in step 63 a filled vial 1 is positioned at a preselected calibration starting position, $P_O$. This is accomplished by several steps including step 65 where vial 1 is placed randomly on conveyor belt 7 at any location preceding vial position detection device 27, say $P_1$. Computer control 17 operates conveyor belt 7 in step 67 to advance vial 1 a predetermined increment, and, in step 69 checks for a signal from vial position detection device 27 whether or not vial 1 has reached its known position. If not, the position of vial 1 is again incremented.

If vial 1 has reached vial position detection device 27, in step 71 computer control 17 again operates conveyor belt 7 to further advance vial 1 incrementally a predetermined number of steps toward the preselected calibration starting position. The preselected calibration starting position may be any position within interrogation zone 25 moving toward, but still just outside the region where the alternating magnetic field is applied by RF probe 29, for example $P_9$ shown in FIG. 2. Once vial 1 reaches the preselected starting position, computer control 17 stops movement of vial 1.

At this point, in step 73 an NMR measurement is performed with vial 1 in a plurality of successive incremental positions, and each time the measurement results are stored in computer control 17, until vial 1 has reached a position moving away from, but just outside the region where the alternating magnetic field is applied by RF coil 29, for example $P_{15}$ shown in FIG. 2. This is accomplished by several steps including step 75 where an NMR measurement is performed, step 77 where the vial position and results of that measurement are stored, step 79 in which vial 1 is incrementally moved, and step 81 where the current position of vial 1 is checked whether it has reached position $P_{15}$. If it has not, another NMR measurement is performed for this new position, its position and results stored and a further incremental advance effected. If it has, further advancement of vial 1 is stopped.

When incrementing the position of vial 1 for successive NMR measurements, the movement interval or step size should be preselected so as to provide acceptable resolution in the sample reply signal. For example, where glass vials having a volume of 2 ml are to be used, a step size of 0.05 mm provides optimal resolution.

Upon completion of step 81, processor 19 then examines in step 83 each stored reply signal and determines the position of vial 1 at which the sample reply signal is at its maximum, $P_M$. One exemplary method by which this position may be determined is by plotting all saved data as a graph with position on the x-axis and signal amplitude on the y-axis. A range of positions then may be identified in association with an acceptable range of maximum sample reply signals, and its center point taken as the position $P_M$. The ordinarily skilled artisan will appreciate other acceptable methods for identifying the position $P_M$.

Once position $P_M$ is known, it is stored in computer control 17 in step 85 as an offset. When, as described hereinbefore regarding the general operation of NMR check weighing system 3, computer control system 17 tracks the motion of conveyor belt 7 as vial 1 is advanced to position $P_M$, processor 19 retrieves this offset, and triggers the AC current to RF probe 29 when the sample is located at the position within the interrogation zone with the output signal characteristic at its maximum.

It will be understood that the embodiments described herein are merely exemplary and that a person skilled in the art may make many variations and modifications without departing from spirit and scope of the invention. The various embodiments may be practiced in the alternative, or in combination, as appropriate. All such modifications and variations are intended to be included within the scope of the invention as defined in the appended claims.

I claim:

1. A magnetic resonance method for determining the mass of non-continuous and discrete samples in a production line, each non-continuous and discrete sample having a net magnetisation capability, comprising the steps of:

applying a first magnetic field in a first direction in an interrogation zone for creating a net magnetisation within a first sample having unknown mass located within the interrogation zone;

applying an alternating magnetic field in a second direction in the interrogation zone in order to temporarily change the net magnetisation of the first sample located within the interrogation zone;

monitoring energy emitted by the first sample as the net magnetisation of the sample returns to its original state and generating an output signal having a characteristic, which is proportional to the energy emitted;

said step of applying an alternating magnetic field including the step of triggering the application of the alternating magnetic field when the first sample is located at a selected position within the interrogation zone where the output signal characteristic is at its maximum;

comparing the output signal characteristic with corresponding data obtained from at least one similar non-continuous and discrete second sample of known mass; and determining the unknown mass of the first sample.

2. The method according to claim 1, wherein said step of applying an alternating magnetic field is performed by triggering a processor with said step of triggering including the step of calibrating the processor prior to production operation of the production line.

3. The method according to claim 2 wherein said step of calibrating the processor includes the steps of performing a magnetic resonance measurement on the second sample at each of the plurality of selected positions as the second sample is moved through the region of the alternating magnetic field, and determining the location of the second sample when the second sample is located at a selected position within the interrogation zone when the output signal characteristic that is representative of the second sample is at its maximum.

4. The method according to claim 3 wherein during magnetic resonance measurement the second sample is moved through the region of the alternating magnetic field from a first side to a second side, and said step of calibrating the processor further includes the step of positioning the second sample at a preselected calibration starting position outside of the first side of the region of the alternating magnetic field.

5. The method according to claim 4, wherein said step of positioning the second sample further includes the step of detecting when the second sample reaches a known position and advancing the second sample to the preselected calibration starting position.

6. The method according to claim 4, wherein said step of performing a magnetic resonance measurement on the second sample includes the step of performing a plurality of magnetic resonance measurements until the second sample is positioned outside of the second side of the region of the alternating magnetic field.

7. The method according to claim 3, wherein the output signal characteristic is current amplitude, and said step of determining the location of the second sample determines when the first sample is located at a selected position within the interrogation zone and when the output signal current representative of the first sample is at its maximum.

8. The method according to claim 7, wherein said step of calibrating the processor further includes the step of storing an offset for triggering the application of an alternating magnetic field when the first sample is located at a selected position within the interrogation zone and when the output signal, current representative of the first sample is at its maximum.

9. A method of calibrating a magnetic resonance method, for determining the unknown mass of non-continuous and discrete production samples in a production line, each non-continuous and discrete production sample having a net magnetisation capability, the production line having a magnetic resonance interrogation zone with a first magnetic field and an alternating magnetic field, comprising the steps of:

performing a nuclear magnetic resonance measurement on a calibration sample of known mass at each of a plurality of selected positions as the calibration sample is moved through the region of the alternating magnetic field prior to production operation of the production line; and determining the location of the calibration sample when the calibration sample is located at one of the plurality of selected positions within the interrogation zone, which produces an output signal that is proportional to the maximum signal energy emitted by the calibration sample undergoing a nuclear magnetic resonance measurement.

10. The method according to claim 9, wherein during the step of performing a nuclear magnetic resonance measurement on the calibration sample, the calibration sample is moved through the region of the alternating magnetic field from a first side to a second side, and said step of performing a nuclear magnetic resonance measurement on the calibration sample further includes the step of positioning the calibration sample at a preselected calibration starting position located outside of the first side of the region of the alternating magnetic field.

11. The method according to claim 10, wherein said step of positioning the calibration sample further includes the step of detecting when the calibration sample reaches one of the plurality of selected positions and advancing the calibration sample to the preselected calibration starting position.

12. The method according to claim 11, wherein said step of performing a magnetic resonance measurement on the calibration sample includes the step of performing a plurality of magnetic resonance measurements until the calibration sample is positionally located outside of the, second side of the region of the alternating magnetic field.

13. The method according to claim 9, wherein said step of determining the location of the calibration sample determines when the production sample is located at one of the plurality of selected positions within the interrogation zone and when the output signal current amplitude which is representative of the production sample is at its maximum.

14. The method according to claim 13, further including the step of storing an offset which triggers the application of an alternating magnetic field when the production sample is located at one of the plurality of selected positions within the interrogation zone and when the output signal current representative of the production sample is at its maximum.

* * * * *